United States Patent [19]

Bastioli et al.

[11] Patent Number: 5,384,170
[45] Date of Patent: Jan. 24, 1995

[54] LAMINATED FILM WITH A STARCHY MATRIX AND LOW PERMEABILITY AND METHODS FOR ITS PRODUCTION

[75] Inventors: Catia Bastioli, Novara; Vittorio Bellotti, Fontaneto D'Agogna; Giancarlo Romano, Novara; Maurizio Tosin, Serravalle Sesia, all of Italy

[73] Assignee: Novamont S.P.A., Milan, Italy

[21] Appl. No.: 82,348

[22] Filed: Jun. 24, 1993

Related U.S. Application Data

[63] Continuation of Ser. No. 741,131, Aug. 7, 1991, abandoned.

[30] Foreign Application Priority Data

Aug. 9, 1990 [IT] Italy .................. 67634A90

[51] Int. Cl.⁶ .............................................. B29D 22/00
[52] U.S. Cl. ............................ 428/34.1; 428/500; 428/516; 524/52
[58] Field of Search ................ 428/34.1, 500, 516; 524/52, 47

[56] References Cited

U.S. PATENT DOCUMENTS

| | | |
|---|---|---|
| 3,652,542 | 3/1972 | Hjermstad . |
| 4,673,438 | 6/1987 | Wittwer . |
| 4,863,655 | 9/1989 | Lacourse et al. ............... 264/53 |
| 4,900,361 | 2/1990 | Sachetto et al. ............... 106/213 |
| 5,035,930 | 7/1991 | Lacourse et al. ............. 428/35.6 |
| 5,043,196 | 8/1991 | Lacourse et al. ............. 428/35.6 |
| 5,095,054 | 3/1992 | Lay et al. ........................ 524/47 |
| 5,254,607 | 10/1993 | McBride et al. ................ 524/52 |
| 5,258,430 | 11/1993 | Bastioli et al. ................. 524/52 |
| 5,292,782 | 3/1994 | Bastioli et al. ................. 524/52 |

FOREIGN PATENT DOCUMENTS

| | | |
|---|---|---|
| 0032802 | 1/1981 | European Pat. Off. . |
| 0282451 | 3/1988 | European Pat. Off. . |
| 0326517 | 8/1988 | European Pat. Off. . |
| 0327505 | 1/1989 | European Pat. Off. . |
| 0298920 | 2/1989 | European Pat. Off. . |
| 0391853 | 3/1990 | European Pat. Off. . |
| 0404723 | 6/1990 | European Pat. Off. . |
| 0404727 | 6/1990 | European Pat. Off. . |
| 0404728 | 6/1990 | European Pat. Off. . |
| 0304401 | 7/1990 | European Pat. Off. . |
| 0407350 | 7/1990 | European Pat. Off. . |
| 0408501 | 7/1990 | European Pat. Off. . |
| 0408502 | 7/1990 | European Pat. Off. . |
| 0408503 | 7/1990 | European Pat. Off. . |
| 0409781 | 7/1990 | European Pat. Off. . |
| 0409782 | 7/1990 | European Pat. Off. . |
| 0409783 | 7/1990 | European Pat. Off. . |
| 0409788 | 7/1990 | European Pat. Off. . |
| 0409789 | 7/1990 | European Pat. Off. . |
| 0388924 | 9/1990 | European Pat. Off. . |
| 0400532 | 12/1990 | European Pat. Off. . |
| 2190093 | 3/1986 | United Kingdom . |
| 8802313 | 3/1988 | United Kingdom . |
| WO90/10671 | 9/1990 | WIPO . |
| WO91/02023 | 2/1991 | WIPO . |
| WO91/02024 | 2/1991 | WIPO . |
| WO91/02025 | 2/1991 | WIPO . |

OTHER PUBLICATIONS

Chemical Abstracts, vol. 7, No. 8, p. 47, Abstract No. 60151n, F. H. Otey et al., "Starch-based blown films" (Aug. 24, 1987).
Otey, F. H. et al., Ind. Eng. Chem. Res. 26(8):1659–63 (1987), "Starch-Based Blown Films".

Primary Examiner—Edith Buffalow
Attorney, Agent, or Firm—Brian Cave

[57] ABSTRACT

A laminated film including at least one first layer of a polymeric material which has a starchy matrix and is insoluble in water or at most expands in water, constituted by destructured starch and an olefinic copolymer and a second layer of a hydrophobic material adhering to the first. Applications are for the packaging of food products and for colostomy containers, for which a very effective barrier against gases and vapours is needed.

13 Claims, No Drawings

LAMINATED FILM WITH A STARCHY MATRIX AND LOW PERMEABILITY AND METHODS FOR ITS PRODUCTION

This is a continuation of U.S. application Ser. No. 07/741,131, filed Aug. 7, 1991, now abandoned.

DESCRIPTION

The present invention relates in general to biodegradable films based on starchy materials and in particular to a film which is substantially insoluble in water and suitable for forming an effective varrier against liquids, gases and vapours, at least for a certain period of time, and which at the same time is rapidly biodegradable after use.

Patent application No. EP-A-0 327 505 describes polymeric materials based on destructured starch and a synthetic thermoplastic polymeric material, which are useful, in particular, for the production of molded articles having better dimensional stability after exposure to moisture than corresponding articles made of starch alone.

More specifically, as regards the production of films, self-supporting and biodegradable flexible films formed from compositions including starchy substances and an ethylene-acrylic acid copolymer are known from EP-A-0 032 802.

The Applicant's European patent No. 90011070.1 describes biodegradable films formed from compositions including starchy substances and an ethylene-vinyl alcohol copolymer.

These films have good resistance to tearing and to dissolving in the presence of water and can thus be used to replace conventional, non-biodegradable synthetic plastics materials for a wide range of applications. In the presence of water, however, the films tend to swell so that their properties as barriers against the diffusion of gases and vapors are seriously compromised, precluding their use in some applications for which this property is important.

It has been found that films with starchy matrices of the type mentioned above can be coated with a hydrophobic material which forms an effective barrier and that the layers of starch-based and hydrophobic materials show good mutual adhesion. It is thus possible to produce a laminated film which is suitable for applications in which an effective barrier against gases and liquids is of critical importance.

A first subject of the invention is a laminated film, characterised in that it includes at least one first layer of a polymeric material which has a starchy matrix and is substantially insoluble in water or at most expands in water, and a second layer of a hydrophobic material adhering to the first.

A polymeric material which has a starchy matrix and is substantially insoluble in water but which at most expands in water, is intended to mean a material which can absorb quantities of water of no more than 40 g per 100 g of the material itself at ambient temperature without dissolving.

Materials suitable for use as the first layer with a starchy matrix include polymeric blends which are obtainable by the fusion of a starch and a synthetic thermoplastic polymer in the presence of water or a plasticiser with a high boiling point under temperature and pressure conditions suitable for producing a homogeneous melt which can be processed as a thermoplastic material.

The synthetic polymeric component includes polymers and copolymers of at least one ethylenically, unsaturated monomer, the polymer or copolymer having repeating units provided with at least a polar group such as hydroxy, alkoxy, carboxy, carboxyalkyl, alkyl carboxy and acetal.

Preferred polymeric components include polyvinyl alcohol and copolymers of an olephin selected from ethylene, propylene, isobutene and styrene with acrylic acid, vinyl alcohol and/or vinyl acetate and mixtures thereof.

The preferred synthetic polymers are ethylene copolymers selected from the group consisting of ethylene-vinyl alcohol, ethylene-acrylic acid, ethylene-vinyl acetate, terpolymers of ethylene-vinyl acetate and vinyl alcohol which can be produced, for example, by the partial hydrolysis of ethylene-vinyl acetate and ethylene-vinyl alcohol copolymers modified by the partial replacement of the functional alcohol groups by oxo or alkylcarbonyl groups.

Preferred ethylene-vinyl alcohol copolymers have ethylene contents of from 10 to 90% by weight, preferably from 10 to 40% by weight (15–50% in moles) and most preferably from 30 to 45% in moles, with a melt flow index between 2 and 50 and preferably between 6 and 20 (210° C., 2.16 Kg). Further preferred characteristics of the polymers are:

| | |
|---|---|
| intrinsic viscosity (in DMSO at 30° C.) | 0.50–09 |
| and preferably | 0.65–0.80 |
| molecular weight distribution Mw/Mn | 1.3–4 |
| molecular weight distribution (GPC in tetrahydrofuran) | |
| melting point | <180° C. |
| and preferably | 160–170° C. |
| degree of hydrolysis* | 90.–99.9% |

*basic hydrolysis and titration of the residual base with acid.

In order to improve their biodegradability, the copolymers may be modified by the replacement of some, preferably from 0.1 to 5% in moles, of their functional alcohol groups by oxo groups or alkylcarbonyl groups in which the alkyl groups contain from 1 to 4 carbon atoms. These modified polymers can be produced from the corresponding ethylene-vinyl alcohol copolymers by known methods.

The ethylene-vinyl acetate polymers used within the scope of the present invention preferably have molar contents of vinyl acetate of from 5 to 90%, preferably from 12 to 80% and the corresponding copolymers modified by the hydrolysis of the acetate group preferably have from 5 to 90% of acetate and hydrolysed groups.

The ethylene-acrylic acid copolymers used may be those described in patent No. EP-A-0 032 802.

It is intended that mixtures of the copolymers indicated above may be used as the polymeric material of the first layer.

The film constituting the first layer of the laminate preferably has a water content due to the intrinsic water content of the starch or to water added during the destructuring stage, of less than 6% and preferably less than 2% by weight (as extruded, before conditioning).

If water has been added in order to facilitate the formation of a fused material which can be processed in an extruder it is necessary, therefore, to reduce the water content by degassing in an intermediate stage of the extrusion, upstream of the filming.

The film constituting the first layer may contain destructured starch and the synthetic polymer in a ratio of from 1:9 to 9:1, preferably from 1:4 to 4:1, but the use of compositions with higher starch contents, in which the synthetic polymer constitutes from about 20 to 40% by weight of the sum of the synthetic polymer and starch is preferred.

The films may include a plasticiser with a high boiling point (boiling point above 150° C.), such as polyethylene glycol, ethylene glycol, propylene glycol, glycerine, polyglicerol, polyethylene glycol sorbitol, mannitol, their acetate, ethoxilate or propoxylate derivatives and mixtures thereof in quantities from 0.05 to 100% and preferably from 0.5 to 30% of the weight of the starch. The presence of the plasticiser is useful both during the destructuring of the starch, particularly with the use of ethylene-vinyl alcohol copolymers, and as regards specific characteristics of the film constituting the first layer.

The nature of the starch used in the material constituting the first layer is not particularly critical and either native starches or physically or chemically modified starches such as starch ethoxylates, starch acetates, cationic starches, oxidised starches and cross-linked starches may be used.

The method of preparing the films constituting the first layer are described in Italian applications Nos. IT 67691-A/89, 67692-A/89, 67413-A/89 and 67666-A89, the contents of which are incorporated by reference.

In a preferred embodiment of the invention, the hydrophobic material constituting the second layer consists essentially of a polymeric coating of polyparaxylylene and/or substitution derivatives thereof, deposited on the film constituting the first layer by the chemical deposition of the vapor phase. The thickness of the second layer may vary within wide limits and, according to the desired barrier properties to be obtained, thicknesses of about 0.01 $\mu$m to about 40 $\mu$m are preferred, preferably from 0.1 to 10 $\mu$m.

The technology of the application of polymeric polyparaxylylene coatings is known and is described, for example, in patent application No. EP-A-0 302 457, but with reference to substrates of a definitely hydrophobic nature.

The paraxylylene radical used corresponds to the formula:

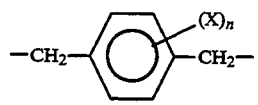

(I)

in which:
X is a $C_1$-$C_6$ alkyl group, a $C_6$-$C_{10}$ aryl group, a $C_7$-$C_{16}$ arylalkyl group, a haloalkyl or haloarylalkyl group, an acetoxy group, an aminoalkyl group, an arylamino group, a cyrano group, an alkoxy group, a hydroxy group, a nitro group, a halogen atom, a sulphonic radical, a sulphonic ester radical, a phosphorus-based substituent, a sulphide group, an alkylsulphoxide group or a hydrogen atom, and
is 0 or a whole number from 1 to 4.

Since their reactivity causes great difficulties in their storage and handling, for practical applications, the preferred starting compounds are the dimers of paraxylylene or (2,2)-paracyclophane and of their derivates conforming to the possible substitutions indicated above.

The dimers of paraxylylene are in fact stable crystalline solids at ambient temperature and can easily be stored and handled. The dimers can be prepared by conventional methods, for example, by the pyrolysis of paraxylylene or from the corresponding paramethylbenzyl trimethylammonium hydroxide by Hofmann degradation.

During the application of the polymeric coating by vapor deposition under vacuum, the paraxylylene dimers are subjected to pyrolytic cracking under vacuum at temperature higher than 400° C. to give reactive radicals of formula (I) which are made to condense on the surface of the substrate producing homopolymers or copolymers of paraxylylene according to the dimer used.

Small quantities of other monomers such as maleic anhydride or chloroprene which polymerise on the surface of the film of material with a starchy matrix may be used with (2,2)-paracyclophane and its derivaties. The bivalent paraxylylene radicals condense and polymerise almost instantaneously on the surface of the first layer forming a compact polymer.

The structural principles of devices for the deposition of vapors of bivalent reactive paraxylylene radicals are known and are described, for example, in Kirk-Othmer Encyclopaedia of Chemical Technology, Third Ed., Volume 24, pages 746–747. Such a device includes an evaporation-cracking furnace in which the (2,2)-paracyclophane or a derivative thereof is inserted, and which is in communication with a deposition chamber which is kept at a temperature lower than the condensation temperature of the specific paraxylylene derivative.

The deposition chamber may conveniently be modified for the purposes of the present application to enable the continuous or semi-continuous deposition of the polymeric coating.

The application of a paraxylylene monomer is compatible with the optional use of agents such as, for example, siloxane compounds or derivatives of phosphorus usually used in the deposition under vacuum technique for promoting adhesion.

By way of example, preferred paraxylylene monomers are chloroparaxylylene, dichloroparaxylylene, cyanoparaxylylene, iodoparaxylylene, fluoroparaxylylene, hydroximethylparaxylylene, ethylparaxylylene, methylparaxylylene, carbomethoxyparaxylylene and mixtures thereof.

In alternative embodiment of the invention, the hydrophobic material used for the second layer is a polymer containing free acid groups, preferably an ethylene-acrylic acid, or an ethylene-acrylic acid-alkyl acrylate copolymer.

For its application to the first layer with a starchy matrix, the polymer is salified by a base, preferably ammonium hydroxide, and is thus made soluble in water. Surfactants, emulsified waxes, silica, polyoxyethylene, polyacrylic acids, polyvinylpyrrolidone, polyvinyl alcohol, etc. may be added to the solution to increase its ability to wet the starchy film and to reduce the stickiness of the coating. The solution thus obtained is spread on the first layer by a tecnique similar to varnishing or spray-coating and undergoes heat treatment at a temperature and for a period of time sufficient to remove the aqueous solvent and eliminate the salifying groups thus producing a polymeric coating which is insoluble in water.

In a further embodiment of the invention, the hydrophobic material used for the second layer is constituted by a polyhydroxyalkanoate polymer, particularly PHB (polyhydroxybutyrate), PHB/V (polyhydroxybutyrate//valerate) lactic acid homopolymers and lactic acids copolymerised with glycolic acids or with Σ-caprolactone, polyethylene-vinyl alcohol, or polyethylene-vinyl acetate.

The coating can be achieved by coextrusion by blowing or casting technology.

These embodiments also produced hydrophobic coatings with good barrier properties and good adhesion to the starchy substrate.

In a further embodiment of the invention the second layer consists of a copolymer of polyvinylpyrrolidone (PVP) or PVP ester with butylacrylate, butyl amylate/methyl methacrylate (85:15–15:85% wt/wt) diethylamminomethyl methacrylate, vinylacetate, vinylacrylate, acrylic acid or acrylic acid polymer, inorganic or organic esters, particularly ammonium salts of acrylic acid or acrylic acid polymer.

Preferably the molar ratio of PVP with respect to the comonomer is from 5 to 60% molar.

The coating is obtained from an aqueous solution or emulsion of the copolymer which is dried to provide a water insoluble film which exhibits good adhesion to the starchy based first layer.

The laminated film according to the invention is particularly suitable for producing containers for faeces, for example, of the type used for colostomy care, in which case, the layer of hydrophobic material prevents unpleasant smells from escaping for at least several hours, and for the packaging of foods with high water contents in general.

The laminated film according to the invention will be described further with reference to the following examples.

EXAMPLE 1

Preparation of the First Starchy Layer

A composition having the following composition was prepared:
- 42% by weight of Globe 03401 Cerestar (registered trade mark) starch which had not been dried and had an intrinsic water content of 11% by weight,
- 39% by weight of an ethylene-vinyl alcohol copolymer with a molar ethylene content of 42%, intrinsic viscosity (DMSO, 30° C.) 0.39, Mw/Mn 3.6, melting point 164° C., degree of hydrolysis 99.3, melt flow index (230° C., 2.16 kg) 20;
- 12.8% by weight of glycerine,
- 3.2% by weight of water,
- 3% by weight of EAA 5981 copolymer (Dow Chemical).

The components were supplied by a gravimetric batching plant to a Baker Perkins MPC/V-30 extruder with a double-screw unit divided into two regions with a screw diameter of 30 mm and a screw-length/diameter ratio (L/D) of 10:1 connected to a single-screw diameter of 30 mm and an L/D ratio of 8:1, divided into three regions. The capillary nozzle had a diameter of 4.5 mm. The extrusion temperature was kept within the range from 120°–180° C. in the double-screw region of the extruder and within the range from 170° to 140° C. in the single-screw region.

The extrusion produced was transformed into pellets and processed by blow extrusion at about 160° C. to produce a film.

EXAMPLE 2-3

A piece of the film produced according to Example 1 having dimensions of 30 cm×30 cm was inserted in the deposition chamber of a commercially-available laboratory deposition plant. 0.4 grams of dichloro-di-p-xylylene were located into the evaporation section. The dichloro-di-p-xylylene was evaporated under vacuum at a pressure of 0.05 mm Hg at 230° C.

The divalent chloro-p-xylylene radical was kept at 680° C. and then allowed to polymerise on the cold surface of the film for two different periods, producing the thicknesses given in the Table:

| Example | Thickness of the coating ($\mu$m) | Permeability* to water vapour |
|---|---|---|
| 1 | 0 | 1800 |
| 2 | 1.5 | 102 |
| 3 | 1 | 43 |

*Permeability expressed in g per 30 $\mu$m/m$^2$ per 24 h, determined at 30° C. and 90% relative humidity.

EXAMPLE 4

A 10% aqueous solution of ethylene-acrylic acid (20% acrylic acid) was prepared and its pH was brought to 10 in the presence of ammonia.

A sample of the film of Example 1 with dimensions of 10 cm ×20 cm×60 $\mu$m was immersed in the solution for 10' and then dried at ambient temperature for 2 hours. The permeability of this film at 38° C. and 90% relative humidity was 390 g per 30 $\mu$m/m$^2$ per 24 h against 1800 g per 3 $\mu$m/m$^2$ per 24 h for the untreated film.

This treatment also makes the film more transparent.

We claim:

1. A laminated film, comprising at least one first layer of polymeric material which has a starchy matrix and is insoluble in water, and a second layer of hydrophobic material adhering to the first layer, wherein the polymeric material comprises a composition including destructured starch and a synthetic thermoplastic polymer, said synthetic thermoplastic polymer being selected from the group consisting of (a) polyvinyl alcohol and (b) copolymers of an olefin selected from the group consisting of ethylene, propylene, isobutene and styrene with acrylic acid, vinyl alcohol or vinyl acetate, the polymeric material further including a high boiling plasticiser and having a water content prior to conditioning of no more that 6% by weight.

2. A laminated film according to claim 1, wherein the polymeric material comprises a composition including destructured starch and wherein said copolymer is selected from the group consisting of ethylene-vinyl alcohol, ethylene-vinyl alcohol modified by the replacement of some of the hydroxyl groups by oxo or alkyl carbonyl groups, ethylene-acrylic acid, ethylene-vinyl acetate, terpolymers of ethylene-vinyl alcohol-vinyl acetate and mixtures thereof.

3. A laminated film according to claim 2, wherein the ethylene copolymer is ethylene-vinyl alcohol with an ethylene content of from 15 to 50% in moles.

4. A laminated film according to claim 1 wherein the ethylene copolymer comprises ethylene-vinyl acetate having a molar content of vinyl acetate of from 12 to 80%.

5. A laminated film according to claim 1 wherein the synthetic thermoplastic polymer in the first layer is an ethylene copolymer in a ratio by weight of starch: copolymer from 1:4 to 4:1.

6. A laminated film according to claim 1, wherein the second layer is formed by a polymer or a copolymer of a paraxylylene monomer having the formula:

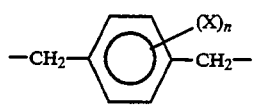 (I)

in which:
X represents a $C_1$–$C_6$ alkyl group, a $C_6$–$C_{10}$ aryl group, a $C_7$–$C_{16}$ arylalkyl group, a haloalkyl or haloarylaklyl group, an acetoxy group, an aminoalkyl group, an arylamino group, a cyano group, an alkoxy group, a hydroxy group, a nitro group, a halogen atom, a sulphonic radical, a sulphonic ester radical, a phosphorus-based substituent, a sulphide group, an alkylsulphoxide group or a hydrogen atom, and
n is 0 or a whole number from 1 to 4.

7. A laminated film according to claim 6, wherein the paraxylylene monomer is selected from the group consisting of chloroparaxylylene, dichloroparaxylylene, cyanoparaxylylene, iodoparaxylylene, fluoroparaxylylene, hydroximethylparaxylylene, ethylparaxylylene, methylparaxylylene, aminomethylparaxylene, carbomethoxyparaxylylene and mixtures thereof.

8. A laminated film according to claim 1 wherein the hydrophobic material of the second layer is a polymer containing free acid groups.

9. A laminated film according to claim 6 wherein the polymer including free acid groups is an ethylene-acrylic acid or an ethylene-acrylic acid-alkylacrylate copolymer.

10. A laminated film according to claim 1 wherein the hydrophobic material of the second layer is a polyhidroxyalkanoate polymer, a lactic acid homopolymer, a copolymer of lactic acids copolymerised with glycolic acids or with $\Sigma$-caprolactone, polyethylene-vinyl alcohol, or polyethylene-vinyl acetate.

11. A laminated film according to claim 1 wherein the second layer comprises a copolymer of polyvinylpyrrolidone (PVP) or PVP ester with butylacrylate, butylacrylate/methylmethacrylate, diethylaminomethyl methacrylate, vinylacetate, acrylic acid or acrylic acid polymer, esters of acrylic acid or esters of acrylic acid polymer.

12. A laminated film according to claim 1, further processed to form a container for feces.

13. A laminated film according to claim 1, further processed to form a packaging for food products.

* * * * *